(12) United States Patent
Li et al.

(10) Patent No.: US 9,301,805 B2
(45) Date of Patent: Apr. 5, 2016

(54) SYSTEMS AND METHODS FOR PERFORMING DIGITAL HOLOGRAPHY

(75) Inventors: Guifang Li, Oviedo, FL (US); Bahaa Saleh, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 734 days.

(21) Appl. No.: 13/417,822

(22) Filed: Mar. 12, 2012

(65) Prior Publication Data

US 2012/0232535 A1 Sep. 13, 2012

Related U.S. Application Data

(60) Provisional application No. 61/451,766, filed on Mar. 11, 2011.

(51) Int. Cl.
| | |
|---|---|
| *A61B 18/20* | (2006.01) |
| *G01B 9/021* | (2006.01) |
| *G03H 1/26* | (2006.01) |
| *G03H 1/04* | (2006.01) |
| *G03H 1/08* | (2006.01) |

(52) U.S. Cl.
CPC .............. *A61B 18/20* (2013.01); *G03H 1/0443* (2013.01); *G03H 1/0866* (2013.01); *G03H 2001/0458* (2013.01); *G03H 2210/62* (2013.01); *G03H 2225/36* (2013.01); *G03H 2226/13* (2013.01)

(58) Field of Classification Search
CPC ..... G03H 2001/0033–2001/0454; G03H 1/00; G03H 2226/11–2226/13; G03H 2225/36; G03H 2210/62; G03H 1/0866; A61B 3/107; A61F 9/008
See application file for complete search history.

(56) References Cited

PUBLICATIONS

Tahara et al., "Comparative evaluation of the image-reconstruction algorithms of single-shot phase-shifting digital holography," Journal of Electronic Imaging 21(1), (Jan.-Mar. 2012).*
Zhang, Xie, Li, Ye, and Saleh, "Single-shot phase-shifting digital holography," Optical Engineering 53(11), 112316 (Nov. 2014).*
Amin, et al. "A hybrid IQ imbalance compensation method for optical OFDM transmission", Optics Express, 18(5):4859-4866, 2010.
Biener, et al "Optical torques guiding cell motility", Optics Express, 17(12):9724-9732, 2009.
Chen, et al. "Acquired Resistance to Small Molecule ErbB2 Tyrosine Kianse Inhibitors", Clin Cancer Res, 14:6730-6734, 2008.
Cohen, et al. "Vector statistics of multiply scattered waves in random systems", Physical Review A, 43(10):5749-5752, 1991.
Dogariu, et al. "Optical Traps as Force Transducers: The Effect of Focusing the Trapping Beam through a Dielectric Interface", Langmuir, 16:2770-2778, 2000.

(Continued)

*Primary Examiner* — Gary Jackson
*Assistant Examiner* — Scott T Luan
(74) *Attorney, Agent, or Firm* — William Greener; Bond Schoeneck & King, PLLC

(57) ABSTRACT

In one embodiment, a system and method for performing single-shot digital holography include an optical hybrid assembly configured to receive a reference beam from a light source and another beam, and a balanced detector comprising multiple sensor arrays that are configured to receive outputs of the optical hybrid assembly and simultaneously measure in-phase and quadrature components of an incoming light wavefront that results from interference between the reference beam and the other beam within the optical hybrid assembly to provide a full set of digital holograms in a single exposure.

25 Claims, 4 Drawing Sheets

(56) References Cited

PUBLICATIONS

Ellis, et al. "Optical Polarimetry of Random Fields", Physical Review Letters, 95:203905:1-4), 2005.

Fink "Time Reversal of Ultrasonic Fields—Part I: Basic Principles", IEEE Transactions of Ultrasonics, Ferroelectrics, and Frequency Control, 39(5):555-566, 1992.

Foroozan, et al. "Time-Reversal Ground-Penetrating Radar: Range Estimation with Cramer-Rao Lower bounds", IEEE Transactions on Geoscience and Remote Sensing, 48(1):3698-3708, 2010.

Freund, et al. "Universal polarization correlations and microstatistics of optical waves in random media", Physical Review B, 42(4):2613-2616, 1990.

Gao, et al. "In vivo cancer targeting and imaging with semiconductor quantum dots", Nature Biotechnology, 22 (8):969-976, 2004.

Han, et al. "Theoretical Sensitivity of Direct-Detection Multilevel Modulation Formats for High Spectral Efficiency Optical Communication", IEEE Journal of Selected Topics in Quantum Electronics, 12(4):571-580, 2006.

Hsieh, et al. "Digital phase conjugation of second harmonic radiation emitted by nanoparticles in turbid media", Optics Express, 18(12):12283-12290, 2010.

Hu, et al. "Phosphodiesterase Type 5 Inhibitors Increase Herceptin Transport and Treatment Efficacy in Mouse Metastatic Brain Tumor Models", PLoS One, 5(4):e10108, 2010.

Leith, et al. "Holographic Imagery Through Diffusing Media", Journal of the Optical Society of America, 56(4):523, 1966.

Larmat, et al. "Time-reversal methods in geophysics", Physics Today, 31-35, 2010.

Li "Recent advances in coherent optical communication", Advances in Optics and Photonics, 1:279-307, 2009.

Mateo, et al. "Electronic phase conjugation for impairment compensation in fiber communication systems", Optical Society of America, 2010.

Miller "Shining New Light on Neural Circuits", Science, 314(5806):1674-1676, 2006.

Nahta, et al. "Molecular mechanisms of trastuzumab resistance", Breast Cancer Research, 8:215, 2006.

Vellekoop, et al. "Scattered light fluorescence microscopy: imaging through turbid layers", Optics Letters, 35(8):1245-1247, 2010.

Wang, et al. "Ballistic 2-D imaging through scattering walls using an ultrafast optical Kerr gate", Science, 253(5021):769-771, 1991.

Yaqoob, et al. "Optical phase conjugation for turbidity suppression in biological samples", Naturephotonics, 2(2):110-115, 2008.

Yamaguchi, et al. "Image formation in phase-shifting digital holography and applications to microscopy", Applied Optics, 40(34):6177-6186, 2001.

Yariv, et al. "Phase Conjugate Optics and Real-Time Holography", IEEE Journal of Quantum Electronics, 14(9):650-660, 1978.

Zel'Dovich, et al. "Phase conjugation in stimulated scattering", Sov. Phys. Usp., 25(10):713-737, 1982.

Zhang "Three-dimensional microscopy with phase-shifting digital holography", Optics Letters, 23(15):1221-1223, 1998.

Cui, et al, "Implementation of digital optical phase conjugation system and its application to study the robustness of turbidity suppression by phase conjugation", Feb. 15, 2010; vol. 18, No. 4; Optics Express; pp. 3444-3455.

Ichirou Yamaguchi; "Phase-shifting digital holography", Optics Letters, vol. 22, No. 16; Aug. 15, 1997; pp. 1268-1270.

* cited by examiner

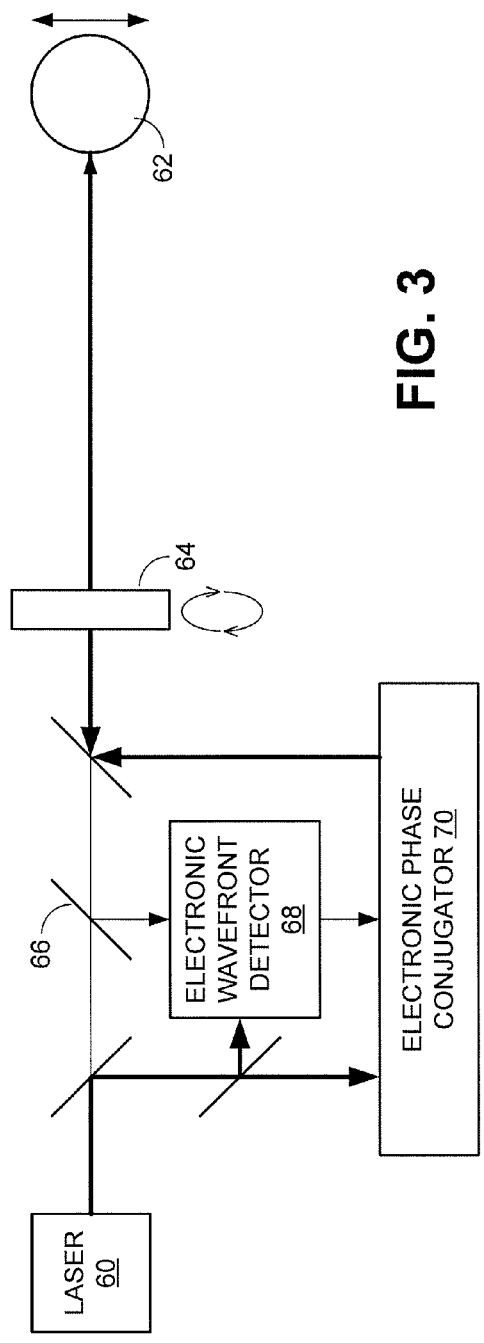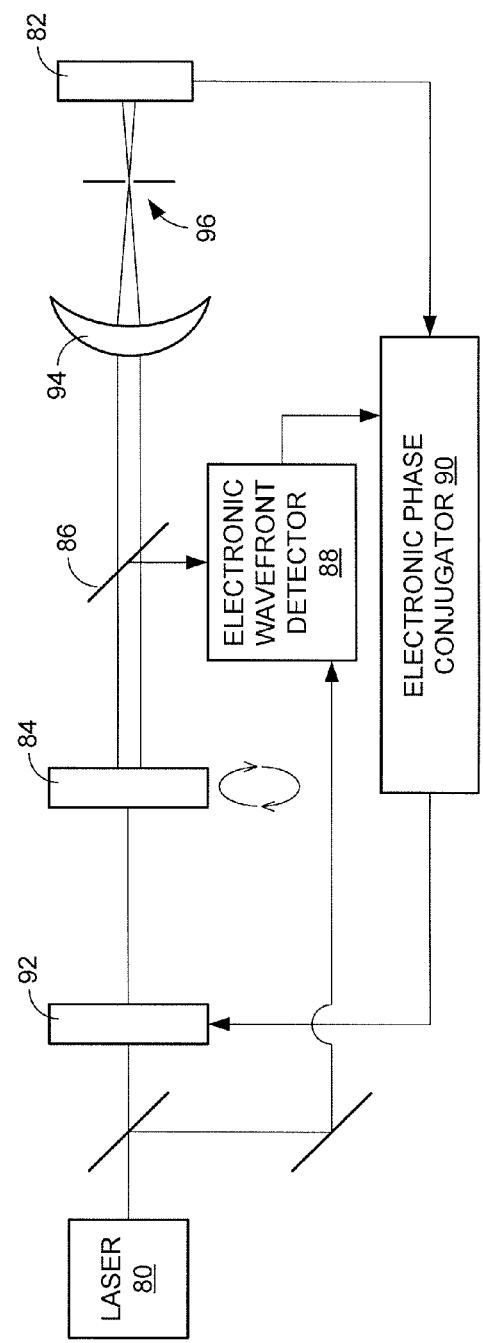

SYSTEMS AND METHODS FOR PERFORMING DIGITAL HOLOGRAPHY

CROSS-REFERENCE TO RELATED APPLICATION(S)

This application claims priority to U.S. Provisional Application Ser. No. 61/451,766 filed Mar. 11, 2011, which is hereby incorporated by reference herein in its entirety.

BACKGROUND

Ever since its invention more than half a century ago, holography has been considered as a tool for three-dimensional (3D) imaging. In conventional holography, photographic films are used to record the holograms, which require chemical processing and significant investments of time. Reconstruction of the 3D images is also inconvenient, requiring proper illumination.

Recent trends in holography have focused on digital techniques for both recording and reconstruction. Off-axis digital holography is one such technique that has received much attention in recent years. In off-axis digital holography, the hologram is captured by a charge-coupled device (CCD) and reconstructed by virtual propagation in the software domain by a computer. Although off-axis digital holography can be used to create holograms of a target object, the method is suboptimal for two reasons. First, off-axis digital holography wastes the resolution of the CCD because of the necessity of recording carrier fringes produced by the angular separation between the object and reference beams. Second, the size of the object or reconstructed image is limited by the presence of the zero-order and conjugate images.

Because of those limitations, it is desirable to record in-line holograms using digital holography. This can be accomplished using phase-shift digital holography in which a piezoelectric transducer mirror is adjusted between exposures to shift the phase of the object wavefront. While phase-shift digital holography is well suited for static objects, its application to dynamic objects has been limited because it requires recording each phase-shifted hologram at a different time, and the object and reference beams do not share a common path. The non-common-path nature makes phase-shift digital holography susceptible to vibrations.

In view of the above discussion, it can be appreciated that it would be desirable to have a system or method for performing digital holography that avoids one or more of the drawbacks described above.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 3 is a schematic diagram of single-shot digital holography being used to track a moving target object.

FIG. 4 is a schematic diagram of single-shot digital holography being used to focus an amplified beam on a target object.

DETAILED DESCRIPTION

As described above, it would be desirable to have a system or method for performing digital holography that avoids one or more of the drawbacks described above. Described herein are systems and methods for performing digital holography in a single exposure. Accordingly, the disclosed digital holography may be described as "single-shot" digital holography. In some embodiments, the single-shot digital holography can be used to perform real-time wavefront measurement that enables backward light propagation.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
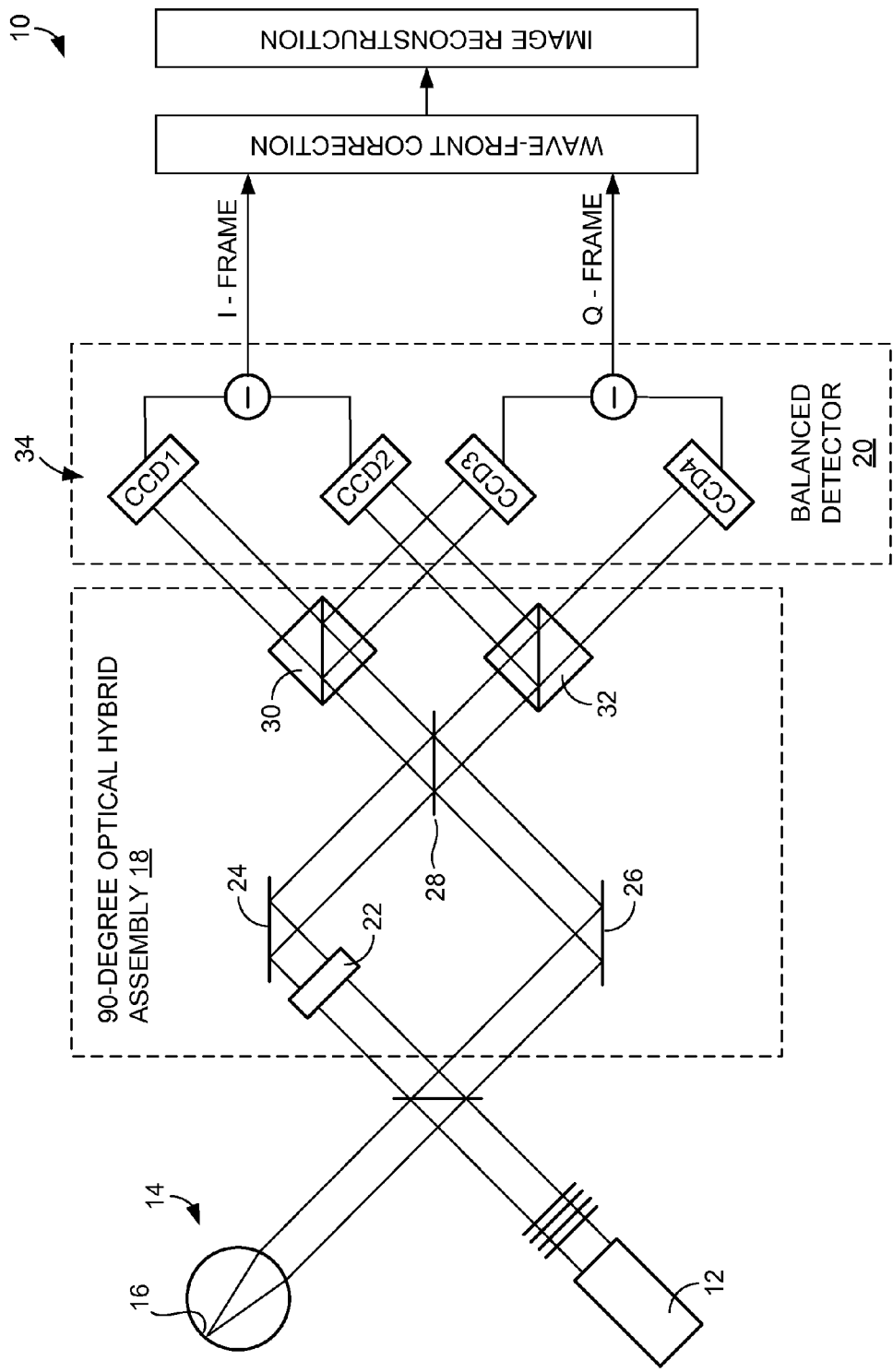
FIG. 1 is a block diagram of an embodiment of single-shot digital holography system.

FIG. 1 illustrates an embodiment of system 10 for performing single-shot digital holography. The system 10 can be used to measure the wavefront that results from interference between the light (i.e., a reference beam) of a light source, in the form of a laser 12, and light (i.e., an object beam) from a target object 14, which in the example of FIG. 1 is the retina 16 of an eye. As is shown in the figure, the system 10 includes a free-space, 90-degree optical hybrid assembly 18 and a balanced detector 20. As is apparent in this figure, the 90-degree optical hybrid assembly 18 comprises a quarter-wave plate 22, mirrors 24 and 26, a half mirror 28, and polarization beam splitters 30 and 32. The balanced detector 20 comprises four sensor arrays 34. In the example embodiment, the sensor arrays 34 are charged-couple device (CCD) sensor arrays CCD1-CCD4.

The system 10 performs the single-shot digital holography technique based on coherent detection using the 90-degree optical hybrid assembly 18. The outputs of the 90-degree optical hybrid assembly 18 are fed into the balanced detector 20 to measure two orthogonal quadratures (i.e., the real and imaginary parts) of the incoming light wavefront (i.e., the intensity and phase distribution of the light as a function of x and y) that results from interference between the reference and object beams, thereby providing a full set of digital holograms in a single exposure. The 90-degree optical hybrid assembly 18 therefore performs the function of combining the object beam with the reference beam and simultaneously providing four copies of the reference beam with successive phase shifts to interfere with the object beam wavefront. Notably, such a result can only be obtained using phase-shifting digital holography (PSDH) by performing four separate exposures. The balanced detection scheme made possible by the system 10 removes zero-order background of the holograms and provides a 3 dB signal-to-noise ratio (SNR) improvement.

The polarization of both the object beam ($\vec{U}^{\|}_o + \vec{U}^{\perp}_o$) and the reference beam ($\vec{U}^{\|}_R + \vec{U}^{\perp}_R$) are adjusted to be approximately 45° with respect to the polarizing beam splitters 30, 32 so that $|\vec{U}^{\|}_o| \approx |\vec{U}^{\perp}_o|$ and $|\vec{U}^{\|}_R| \approx |\vec{U}^{\perp}_R|$. In cases in which the target object is contained within biological tissue, as when the target object is a cancer cell (see, e.g., FIG. 3), the light from the object will deviate from the original polarization of the light source 12 due to birefringence and scattering within the tissue. A linear polarizer can be inserted to ensure that only the polarization component aligned with that of the reference beam gets through. When the reference beam passes through the quarter-wave plate 22, its parallel and perpendicular components experience a relative phase shift of 90° to become $\overline{U}^\parallel_R + j\overline{U}^\perp_R$. The output after the half mirror 28 is given by:

$$\frac{1}{\sqrt{2}}\begin{bmatrix} 1 & 1 \\ -1 & 1 \end{bmatrix} \cdot \begin{bmatrix} \overline{U}^\parallel_O + \overline{U}^\perp_O \\ \overline{U}^\parallel_R + j\overline{U}^\perp_R \end{bmatrix} = \begin{bmatrix} (\overline{U}^\parallel_O + \overline{U}^\perp_O) + \\ (\overline{U}^\parallel_R + j\overline{U}^\perp_R) \\ -(\overline{U}^\parallel_O + \overline{U}^\perp_O) + \\ (\overline{U}^\parallel_R + j\overline{U}^\perp_R) \end{bmatrix}, \quad [\text{Equation 1}]$$

where $\dfrac{1}{\sqrt{2}}\begin{bmatrix} 1 & 1 \\ -1 & 1 \end{bmatrix}$ is the scattering matrix of the half mirror. As a result, the output fields at the four CCDs from top to bottom are given by:

$$\frac{1}{\sqrt{2}} \begin{bmatrix} \overline{U}^\parallel_O + \overline{U}^\parallel_R \\ -\overline{U}^\parallel_O + j\overline{U}^\parallel_R \\ \overline{U}^\perp_O + \overline{U}^\perp_R \\ -\overline{U}^\perp_O + j\overline{U}^\perp_R \end{bmatrix} \quad [\text{Equation 2}]$$

and the intensity at the four CCDs from top to bottom are:

$$\frac{1}{2} \begin{bmatrix} |\overline{U}^\parallel_O|^2 + |\overline{U}^\parallel_R|^2 + \overline{U}^\parallel_O \overline{U}^{\parallel*}_R + \overline{U}^{\parallel*}_O \overline{U}^\parallel_R \\ |\overline{U}^\parallel_O|^2 + |\overline{U}^\parallel_R|^2 - \overline{U}^\parallel_O \overline{U}^{\parallel*}_R - \overline{U}^{\parallel*}_O \overline{U}^\parallel_R \\ |\overline{U}^\perp_O|^2 + |\overline{U}^\perp_R|^2 - j\overline{U}^\perp_O \overline{U}^{\perp*}_R + j\overline{U}^{\perp*}_O \overline{U}^\perp_R \\ |\overline{U}^\perp_O|^2 + |\overline{U}^\perp_R|^2 + j\overline{U}^\perp_O \overline{U}^{\perp*}_R - j\overline{U}^{\perp*}_O \overline{U}^\perp_R \end{bmatrix} \quad [\text{Equation 3}]$$

Without loss of generality, it can be assumed that the complex amplitude of the plane reference wave is real. After balanced detection, the in-phase and quadrature components are $$\begin{bmatrix} 2\overline{U}^\parallel_R \text{Re}(\overline{U}^\perp_O) \\ 2\overline{U}^\perp_R \text{Im}(\overline{U}^\perp_O) \end{bmatrix}, \quad [\text{Equation 4}]$$

containing the real and imaginary parts of the object wavefront. Therefore, the complex field of the object wavefront can be obtained in a single exposure or shot.

The orthogonality of the two quadratures is a direct result of the scattering matrix of the half mirror 22. Since the half mirror 22 is an antisymmetric 3 dB coupler that also must satisfy power conservation, the 90-degree phase relationship among the scattering matrix elements is maintained as a matter of first principles. Even if the splitting ratio of the half mirror $\alpha^2$ is not exactly 50 percent, the scattering matrix for the half mirror 22 is $$\begin{bmatrix} \alpha & \sqrt{1-\alpha^2} \\ -\sqrt{1-\alpha^2} & \alpha \end{bmatrix}$$

and the phase relationship of the two quadratures is maintained.

The imperfection of the components in the 90-degree optical hybrid assembly 18 can be calibrated and compensated. For example, if the reference beam is not exactly 45° with respect to the polarization beam splitters 30, 32 so that $|\overline{U}^\parallel_R| \neq |\overline{U}^\perp_R|$, this imbalance can be calibrated by measuring the CCD outputs with the object beam blocked. The result of the measurement can then be used to appropriately scale the output given by Equation 4. All imperfections and imbalances in the 90-degree optical hybrid assembly 18 are deterministic and can be removed numerically after detection.

The polarization component of the object beam orthogonal to the component measured in FIG. 1 can be split and measured using another coherent image sensor.

The single-shot digital holography described above may not completely solve the coherence issue of fluorescent objects. Even for fluorescence from quantum dots, the excited state lifetime is on the order of 20-50 nanoseconds (ns), which is much faster than the CCD frame rate. One solution to this issue is to use a filter to increase the coherence time of the fluorescence. Another approach is to gate the CCD recording process using a pulsed local oscillator, specifically nanosecond pulses at repetition rates that match the CCD frame rate.

There are many applications for single-shot digital holography, especially when combined with wavefront engineering. When the target object is contained within an inhomogeneous medium, such as biological tissue, the object is a source of optical waves that travel through the medium to the balanced detector. The data recovered from the measured wavefront can then be used to generate another physical wave that is a time-reversed version of the sensed wave. The new wave can then retrace the path of the sensed wave back to the target object. In essence, the new wave is a phase-conjugated version of the sensed wave.

Figure 2:
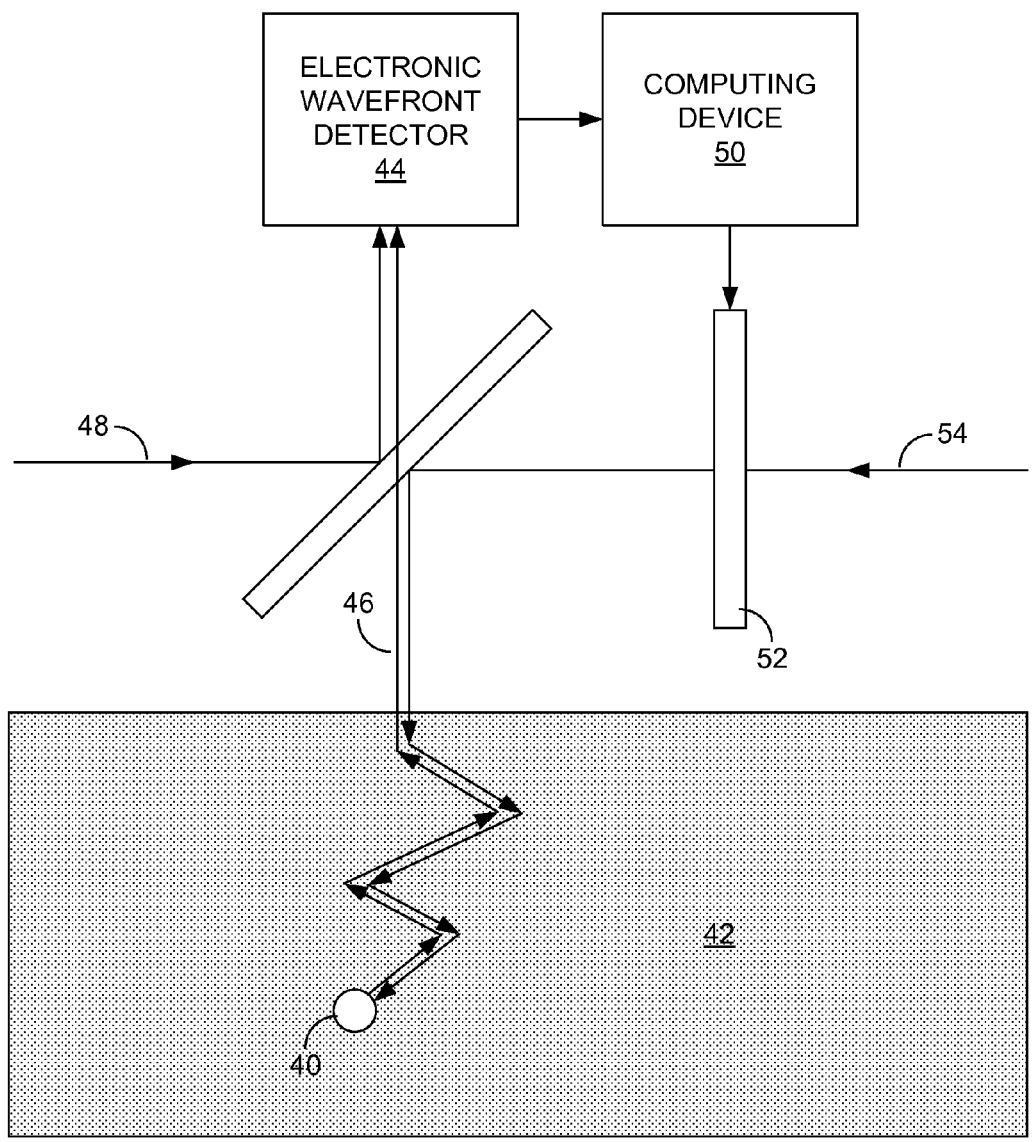
FIG. 2 is a schematic diagram of single-shot digital holography being used to propagate light back to a cell in biological tissue.

FIG. 2 illustrates an example of backward propagation through an inhomogeneous medium. In particular, FIG. 2 illustrates backward propagation to a cell of interest 40 that is contained within biological tissue 42. The approach used in FIG. 2 is based on the use a combination of three techniques: (a) identification of target locations by means of the guided star principle, (b) wavefront sensing by means of single-shot digital holography via real-time coherent detection, and (c) electronic phase conjugation to generate time-reversal, i.e., a wave capable of retracing itself back to its original source.

The cell (or cells) of interest 40 can be fluorescently labeled, for example using a fluorescent dye. Upon excitation by illuminating light (not shown), the cell 40 will fluoresce and that fluorescence will experience multiple scattering as it travels through the tissue 42 until eventually reaching an electronic wavefront detector 44, which can have a configuration similar to that of the single-shot digital holography system 10 shown in FIG. 1. The electronic wavefront detector 44 measures the wavefront by interfering the object beam 46 with a reference beam 48 and provides the measurements to a computing device 50, which can perform electronic phase conjugation on the wavefront to time reverse the wavefront. The computing device 50 can then output the complex conjugate of the wavefront to a spatial light modulator 54, which then imprints the wavefront on a therapeutic beam 54 (i.e., modulates the beam), which can then travel backward through the tissue 42 traversing the same path as the object beam 46 and reach the cell 40. In some embodiments, the therapeutic beam 54 can be a high power beam having either the same or different wavelength as compared to the object beam 46.

Although phase conjugation can be realized by use of nonlinear optics, the efficiency is very low and consequently high power, which may be necessary to perform the desired function, cannot be delivered to the cell 40. Electronic phase conjugation removes the wavelength and efficiency limitation as CCDs responsive in almost all wavelength ranges of interest are available and tunable lasers and modulators are widely available. The input laser power to the spatial modulator can be very high. The wavelength of the electronic phase conjugation signal can be arbitrary so that the signal (fluorescence) can be in the red or green wavelengths and the phase conjugate can be in the near infrared where photodynamic therapy is more effective. Moreover, coherent detection is much more sensitive than nonlinear optical sampling as has already been demonstrated in optical communication. The field of view and resolution of electronic phase conjugation are determined by the CCD/modulator array pixel size and array dimensions.

Single-shot digital holography and electronic phase conjugation has great potential for the treatment of diseases, such as cancer. For example, the drug Herceptin has been used for treating breast cancer because it has been shown to shut down cancerous cell divisions. However, resistance to Herceptin does occur. In such cases, Herceptin can be conjugated with a fluorescent dye to mark the location of the cancer cells, and backward light propagation can be used to kill them with powerful time-reversed optical radiation.

Single-shot digital holography can be used in applications beyond biological applications. Generally speaking, the applications for single-shot digital holography can be classified into two categories. In the first category, the target object is not accessible, for example because the target is an adversary, the target is far way such as in a communication system, or the target is buried in physical or biological structures. For such systems, the coherent wavefront detector can sense a reflected wavefront from the target. FIG. 3 shows a system that conceptually illustrates this first application category. In particular, FIG. 3 simulates the ability of the electronic phase conjugation technology to simultaneously perform wavefront correction as well as pointing and tracking.

In FIG. 3, a laser 60 emits a reference beam toward a moving target object 62, which has a convex surface and an apex upon which light is to be focused as the object moves. Before reaching the object 62, the reference beam passes through a rotating glass plate 64 that represents wavefront distortion that could be created by some natural phenomenon, such as fog. A portion of the light that returns from the object 62 is reflected by a beam splitter 66 and is provided to an electronic wavefront detector 68 that can also be configured like the system 10 shown in FIG. 1. The electronic wavefront detector 68 measures the wavefront by interfering the returning object beam with the reference beam and provides the measurements to an electronic phase conjugator 70, which can output the complex conjugate of the wavefront back to the object 62.

In the second application category, the target object is accessible, for example, using amplification in a master oscillator power amplifier (MOPA) configuration. For such cases, the coherent wavefront detector can sense forward-propagating wavefronts emitted toward the object. FIG. 4 conceptually illustrates this application category. In that figure, a laser 80 emits a reference beam toward a target object, represented by a light sensor 82. The reference beam is passed through a power amplifier that introduces unknown and time-varying wavefront distortion. The power amplifier is represented in FIG. 4 by a rotating glass plate 84. A portion of the distorted beam is reflected by a beam splitter 86 and is provided to an electronic wavefront detector 88, which again can also be configured like the system 10 shown in FIG. 1. The electronic wavefront detector 88 measures the wavefront by interfering the original reference beam with the distorted reference beam and provides the measurements to an electronic phase conjugator 90, which can output the complex conjugate of the wavefront to a spatial light modulator 92, which modulates the reference beam to account for the distortion added by the power amplifier. Wavefront engineering in this application is not a straightforward phase conjugation process. Instead, it comprises a multiple-input multiple-output (MIMO) optimization where the output power through a pin-hole is used as the cost function. Without electronic wavefront sensing, the only feedback algorithm is the output power through the pin-hole. As a result, the optimization processing is single-input multiple-output (SIMO), which is mathematically underdetermined. With real-time electronic wavefront sensing, the optimization process can be mathematically well-defined and robust.

As is further shown in FIG. 4, an aberrating lens 94 introduces additional wavefront distortion downstream, which for example could be provided by a focusing lens of the real world system. In addition, a pinhole aperture 96 is used to determine a cost function that can provide feedback that can be used to maximize power on the detector 82. Such optimization can be performed by algorithms comprised by the electronic phase conjugator 90.

Figure 5:
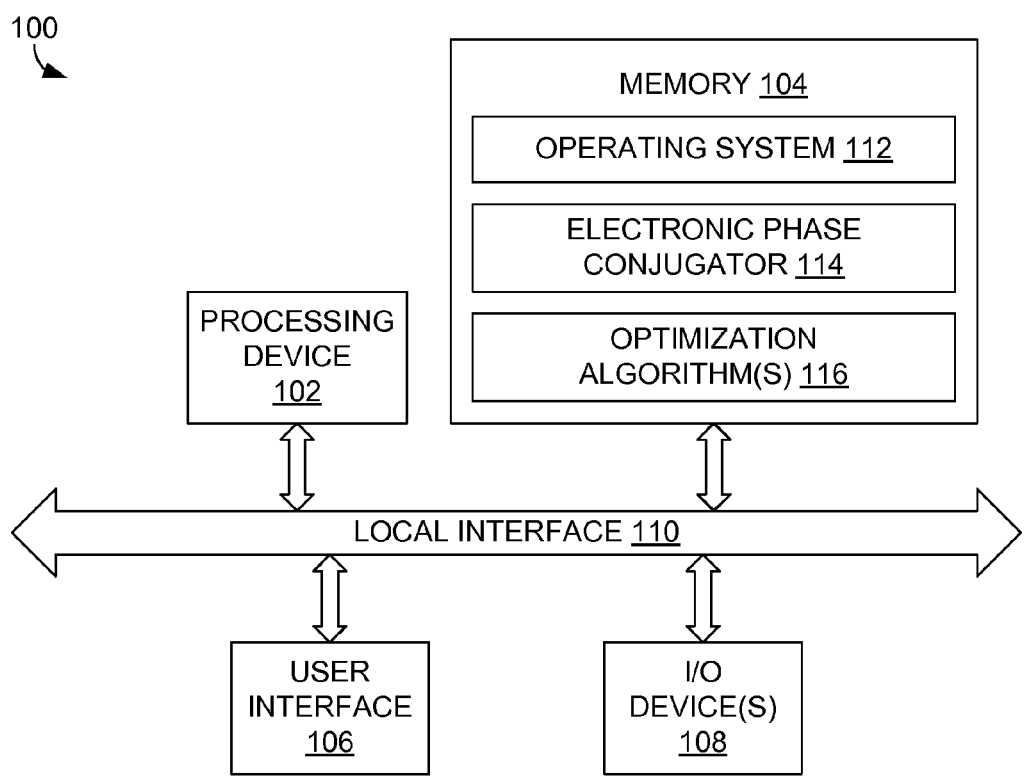
FIG. 5 is a block diagram of a computing device that can be used to perform backward light propagation in a single-shot digital holography scheme.

FIG. 5 illustrates an example configuration for a computing device 100 that can be used to perform at least some of the actions described above. As is shown in FIG. 5, the computing device 100 comprises a processing device 102, memory 104, a user interface 106, and at least one I/O device 108, each of which is connected to a local interface 110.

The processing device 102 can include a central processing unit (CPU) or a semiconductor based microprocessor (in the form of a microchip). The memory 104 includes any one of or a combination of volatile memory elements (e.g., RAM) and nonvolatile memory elements (e.g., hard disk, ROM, tape, etc.). The user interface 106 comprises the components with which a user interacts with the computing device 100, and the I/O devices 108 are adapted to facilitate communications with other devices.

The memory 104 comprises programs (i.e., logic) including an operating system 112, an electronic phase conjugator 114, and one or more optimization algorithms 116. The electronic phase conjugator 114 is configured to perform electronic phase conjugation on measured wavefronts (e.g., measured using single-shot digital holography) to time reverse the wavefronts. The complex conjugate of the wavefronts can then be provided to another component, such as a spatial light modulator. The optimization algorithms 116 can be configured to optimize (e.g., maximize) a signal based upon feedback from a suitable component, such as a light detector.

The invention claimed is:

1. A system for performing single-shot digital holography, the system comprising:
   an optical hybrid assembly configured to receive a reference beam from a light source and another beam; and
   a balanced detector comprising multiple sensor arrays that are configured to receive outputs of the optical hybrid assembly and simultaneously measure in-phase and quadrature components of an incoming light wavefront that results from interference between the reference beam and the other beam within the optical hybrid assembly to provide a full set of digital holograms in a single exposure.

2. The system of claim 1, wherein the other beam is an object beam from a target object.

3. The system of claim 1, wherein the other beam is a distorted beam that results after the reference beam passes through a distorting medium.

4. The system of claim 3, wherein the distorting medium is an amplifier.

5. The system of claim 1, wherein the optical hybrid assembly is a 90-degree optical hybrid assembly.

6. The system of claim 5, wherein the 90-degree optical hybrid assembly comprises a half mirror configured to reflect and to transmit a portion of each of the reference beam and the other beam.

7. The system of claim 6, wherein the 90-degree optical hybrid assembly further comprises two polarization beam splitters configured to adjust the polarization of the reference beam and the other beam by approximately 45 degrees.

8. The system of claim 7, wherein the 90-degree optical hybrid assembly further comprises a quarter-wave plate configured to shift the relative phase of parallel and perpendicular components of the reference beam by approximately 90 degrees.

9. The system of claim 1, wherein the balanced detector comprises four sensor arrays, two of the sensor arrays configured to receive a real part of the wavefront and the other two sensor arrays configured to receive an imaginary part of the wavefront.

10. The system of claim 9, wherein the sensor arrays are charged-couple device (CCD) sensor arrays.

11. The system of claim 1, further comprising an electronic phase conjugator configured to perform electronic phase conjugation on the measured wavefront components to obtain the complex conjugate of the wavefront.

12. The system of claim 11, further comprising a spatial light modulator configured to receive the complex conjugate of the wavefront from the electronic phase conjugator and modulate a further beam with the complex conjugate.

13. A method for performing digital holography, the method comprising:
  receiving a reference beam from a light source and another beam;
  interfering the reference beam and the other beam to generate an interference wavefront and separating the wavefront into its in-phase and quadrature components; and
  simultaneously measuring the in-phase and quadrature components of the wavefront to obtain a full set of digital holograms in a single exposure.

14. The method of claim 13, wherein the other beam is an object beam from a target object.

15. The method of claim 13, wherein the other beam is a distorted beam that results after the reference beam passes through a distorting medium.

16. The method of claim 15, wherein the distorting medium is an amplifier.

17. The method of claim 13, wherein the interfering and separating is performed by a 90-degree optical hybrid assembly.

18. The method of claim 17, wherein the 90-degree optical hybrid assembly comprises a half mirror configured to reflect and to transmit a portion of each of the reference beam and the other beam, two polarization beam splitters configured to adjust the polarization of the reference beam and the other beam by approximately 45 degrees, and a quarter-wave plate configured to shift the relative phase of parallel and perpendicular components of the reference beam by approximately 90 degrees.

19. The method of claim 13, wherein simultaneously measuring comprises simultaneously measuring the in-phase and quadrature components with four sensor arrays with two of the sensor arrays measuring a real part of the wavefront and the other two sensor arrays measuring an imaginary part of the wavefront.

20. A method for performing backward light propagation, the method comprising:
  receiving a reference beam from a light source and an object beam from a target object;
  interfering the reference beam and the object beam to generate an interference wavefront and separating the wavefront into its in-phase and quadrature components;
  simultaneously measuring the in-phase and quadrature components of the wavefront to obtain a full set of digital holograms in a single exposure; and
  performing electronic phase conjugation on the measured wavefront components to obtain the complex conjugate of the wavefront.

21. The method of claim 20, wherein the interfering and separating is performed by a 90-degree optical hybrid assembly.

22. The method of claim 21, wherein the 90-degree optical hybrid assembly comprises a half mirror configured to reflect and to transmit a portion of each of the reference beam and the object beam, two polarization beam splitters configured to adjust the polarization of the reference beam and the object beam by approximately 45 degrees, and a quarter-wave plate configured to shift the relative phase of parallel and perpendicular components of the reference beam by approximately 90 degrees.

23. The method of claim 20, wherein simultaneously measuring comprises simultaneously measuring the in-phase and quadrature components with four sensor arrays with two of the sensor arrays measuring a real part of the wavefront and the other two sensor arrays measuring an imaginary part of the wavefront.

24. The method of claim 20, further comprising modulating a further beam with the complex conjugate of the wavefront so that the further beam propagates backward along a path of the object beam back to the object.

25. The method of claim 24, wherein the object is one or more cells within biological tissue that have been tagged with a fluorescent dye and wherein the further beam is a high power therapeutic beam adapted to kill the cells.

* * * * *